United States Patent
Negrisoli et al.

(10) Patent No.: US 8,623,900 B2
(45) Date of Patent: Jan. 7, 2014

(54) AMINO ALCOHOL DERIVATIVES AND THEIR THERAPEUTIC ACTIVITIES

(75) Inventors: Gianpaolo Negrisoli, Chignolo d'Isola (IT); Renato Canevotti, Chignolo d'Isola (IT); Massimo Previtali, Chignolo d'Isola (IT); Giancarlo Aldini, Milan (IT); Marina Carini, Milan (IT); Marica Orioli, Milan (IT); Giulio Vistoli, Milan (IT)

(73) Assignees: Flamma S.p.A., Chignolo d'Isola (IT); Universita degli Studi di Milano, Milan (IT)

( * ) Notice: Subject to any disclaimer, the term of this patent is extended or adjusted under 35 U.S.C. 154(b) by 0 days.

(21) Appl. No.: 13/519,645

(22) PCT Filed: Dec. 20, 2010

(86) PCT No.: PCT/EP2010/070238
§ 371 (c)(1),
(2), (4) Date: Aug. 28, 2012

(87) PCT Pub. No.: WO2011/080139
PCT Pub. Date: Jul. 7, 2011

(65) Prior Publication Data
US 2012/0316212 A1    Dec. 13, 2012

(30) Foreign Application Priority Data

Dec. 29, 2009 (IT) .............................. MI2009A2317

(51) Int. Cl.
*A61K 31/40* (2006.01)
*A61K 31/417* (2006.01)
*C07D 233/61* (2006.01)
*C07D 207/09* (2006.01)

(52) U.S. Cl.
USPC ......... 514/399; 548/335.5; 548/561; 514/428

(58) Field of Classification Search
USPC ........................ 548/335.5, 561; 514/399, 428
See application file for complete search history.

(56) References Cited

PUBLICATIONS

Guiotto Andrea et al: "Carnosine and carnosine-related antioxidants: A review". Current Medicinal Chemistry, vol. 12 (20), 2005, pp. 2293-2315.*
International Search Report dated Feb. 8, 2011, in corresponding PCT application.
Guiotto Andrea et al: "Carnosine and carnosine-related antioxidants: A review". Current Medicinal Chemistry. Bentham Science Publishers BV. BE LNKD-DOI: 10.2174/0929867054864796. vol. 12. No. 20. Sep. 1, 2005. pp. 2293-2315. XP008106853.
Aldini G. et al: "Carnosine and related dipeptides as quenchers of reactive carbonyl species: From structural studies to therapeutic perspectives", Biofactors, Oxford University Press, Oxford, GB, vol. 24, No. 1-4, Jan. 1, 2005, pp. 77-87, XP009074080.
Vistoli G. et al.,: "Design, Synthesis, and Evaluation of Carnosine Derivatives as Selective and Efficient Sequestering Agents of Cytotoxic Rective Carbonyl Species", CHEMMEDCHEM, vol. 4, 2009, pp. 967-975, XP002589131.

* cited by examiner

*Primary Examiner* — Kamal Saeed
*Assistant Examiner* — Janet L Coppins
(74) *Attorney, Agent, or Firm* — Young & Thompson

(57) ABSTRACT

The present invention relates to amino alcohol derivatives of general formula I:

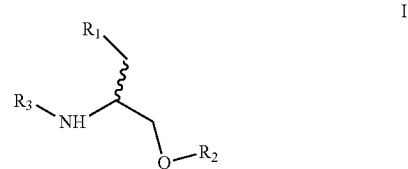

These derivatives possess an interesting activity in that they block the secondary products of lipid oxidative stress, and are consequently suitable for therapeutic use in all disorders related with the presence of reactive carbonyl compounds.

10 Claims, No Drawings

AMINO ALCOHOL DERIVATIVES AND THEIR THERAPEUTIC ACTIVITIES

The present invention relates to amino alcohol derivatives containing nitrogenous heterocyclic groups with metabolic quenching activity towards carbonyl compounds.

PRIOR ART

The influence of oxidative damage on triggering various physiopathological processes, including aging, inflammatory disorders, diabetes, cardiovascular disease and neurodegenerative processes, is unanimously recognised. The main molecular mechanisms responsible for oxidative damage, such as structural damage to proteins, lipids and nucleic acids caused by radical reactive oxygen species, and an altered cell redox state, are also well known [Halliwell B, Gutteridge μM. Free Radicals in Biology and Medicine (2001) Oxford Science Publications, 3rd ed.].

It has also been clarified that some products of lipid oxidation characterised by a keto/aldehyde function act as important cytotoxic oxidative mediators, inducing irreversible structural modifications of the biomolecules, leading to alteration of the cell functions [Uchida K. Free Radic. Biol. Med. 2000; 28:1685-96; Poli G. et al., IUBMB Life. 2000; 50:315-21].

The carbonyl compounds studied include the products of oxidation of polyunsaturated fatty acids, including alpha, beta-unsaturated aldehydes such as 4-hydroxy-trans-2-nonenal (HNE) and acrolein (ACR) [Esterbauer H. et al., Free Radic. Biol. Med. 1991; 11:81-128].

The participation of unsaturated aldehydes in various pathological processes with an oxidative basis has been demonstrated with the use of mono- and polyclonal antibodies [Uchida K. Prog. Lipid Res. 2003; 42:318-43.]. In particular, adducts between HNE and acrolein with proteins have been identified in biopsy and autopsy tissue of patients suffering from diabetes, atherosclerosis, muscular dystrophy, rheumatoid arthritis, cerebral ischaemia, and neurodegenerative diseases such as Alzheimer's disease and Parkinson's disease [Uchida K. Prog. Lipid Res. 2003; 42:318-43; Zarkovic N. Mol. Aspects. Med. 2003; 24:281-91; Zarkovic N. Mol. Aspects. Med. 2003; 24:293-303; M. Carini et al. in "Redox Proteomics: from Protein Modifications to Cellular Dysfunction and Diseases" (Ed. I. Dalle-Donne, A. Scaloni, and A. Butterfield); Wiley InterScience Books from John Wiley & Sons (2005).

The role of HNE as a pathogenetic factor has been demonstrated at molecular level for various disorders, including, for example, fibrosis [Chiarpotto AND. et al., Biofactors. 2005; 24(1-4):229-36], diabetic nephropathy [Furfaro A L. et al. Biofactors. 2005; 24(1-4):291-8], atherosclerotic processes [Leonarduzzi G. et al., Mol Nutr Food Res. 2005 November; 49(11):1044-9], and neurodegenerative disorders [Zarkovic K. Mol Aspects Med. 2003 August-October; 24(4-5):293-303].

It is therefore evident that carbonyl products, especially reactive carbonyl compounds such as HNE, are important targets for the development of a new class of biologically active molecules with carbonyl-quenching activity.

This interest is clearly demonstrated by the considerable number of articles and patents describing compounds with carbonyl-quenching activity, especially particular dipeptide compounds correlated with carnosine [Hipkisss A. R., J. Alzheimer's Dis. 2007, 11, 229-240; Guiotto A. et al. Curr. Med. Chem. 2005, 12, 2293-2315; Vistoli G. et al, Chem. Med. Chem. 2009, 4, 1-10].

DESCRIPTION OF THE INVENTION

The present invention relates to amino alcohol derivatives containing a nitrogen heterocyclic residue which have demonstrated an interesting activity of blocking the secondary products of oxidative lipid stress, in particular those of unsaturated aldehydes such as malondialdehyde and hydroxynonenal, which are known for their contribution to the onset of a considerable number of chronic disorders such as neurodegenerative disorders, chronic inflammatory disorders, cardiovascular disease, and complications of diabetes and cataract. The compounds according to the invention, studied as from the structure of endogenous dipeptide L-carnosine, which is present in some human body tissues and whose activity of quenching unsaturated carbonyl compounds in vitro is well known, have demonstrated a surprisingly greater activity than the dipeptide in quenching model carbonyl compounds, and extremely high metabolic stability if compared with that of the model compound, which makes them suitable for the therapeutic use in all disorders correlated with the presence of reactive carbonyl compounds.

The invention also relates to the use of said compounds for the preparation of medicaments for the treatment or prevention of said disorders.

The compounds of the invention have the general formula I

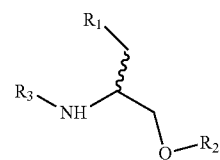

wherein:
   $R_1$ is an optionally condensed, optionally substituted nitrogen heterocyclic ring, containing one or more nitrogen atoms, at least one of which is an —NH— group;
   $R_2$ is hydrogen, straight, branched or cyclic $C_1$-$C_{10}$ alkyl, straight, branched or cyclic $C_1$-$C_8$ alkylcarbonyl, an optionally substituted arylcarbonyl or arylalkylcarbonyl group;
   $R_3$ is a group of formula II

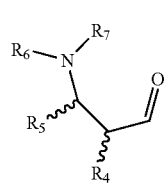

wherein
   $R_4$ and $R_5$, which can be the same or different, are hydrogen; straight or branched $C_1$-$C_8$ alkyl or cyclic $C_3$-$C_7$ alkyl; aryl-$C_1$-$C_5$ alkyl or heteroaryl-$C_1$-$C_5$-alkyl; an aryl or heteroaryl group;
   $R_6$ and $R_7$, which can be the same or different, are hydrogen, straight, branched or cyclic $C_1$-$C_8$ alkyl, straight or branched $C_1$-$C_{20}$ alkylcarbonyl or cyclic $C_3$-$C_7$ alkylcarbonyl optionally containing one or more double bonds, an arylcarbonyl or arylalkylcarbonyl group; straight or branched $C_1$-$C_{10}$ alkyloxycarbonyl or cyclic $C_3$-$C_7$ alkyloxycarbonyl optionally containing one or more double bonds, an aryloxycarbonyl or arylalkyloxycarbonyl group; an amino group, or a group of general formula III

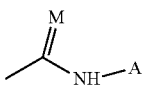

III wherein M is nitrogen, oxygen or sulfur and A is hydrogen or an amino group.

Many compounds of formula I have at least one chiral center, and the invention therefore comprises all the optical isomers of the products of the invention and the mixtures thereof in any proportion, as well as all the possible diastereomers individually taken or in a mixture thereof in any proportion.

$R_1$ is preferably optionally substituted imidazole, pyrrole, pyrazole, indole, isoindole, indazole, benzimidazole; more preferably $R_1$ is an imidazole ring optionally substituted at the 2- or 4-position by a straight, branched or cyclic $C_1$-$C_6$ alkyl group or a halogen atom.

$R_2$ is preferably hydrogen, straight, branched or cyclic $C_1$-$C_8$ alkylcarbonyl, an arylcarbonyl or arylalkylcarbonyl group.

More preferably, $R_2$ is hydrogen.

$R_3$ is preferably a group of formula II

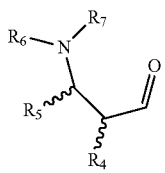

II wherein $R_4$ and $R_5$, which can be the same or different, are hydrogen; straight or branched $C_1$-$C_8$ alkyl or cyclic $C_3$-$C_7$ alkyl; aryl-$C_1$-$C_5$ alkyl or heteroaryl-$C_1$-$C_5$-alkyl; an aryl or heteroaryl group;

$R_6$ and $R_7$, which can be the same or different, are hydrogen, straight or branched $C_1$-$C_{10}$ alkylcarbonyl or cyclic $C_3$-$C_7$ alkylcarbonyl optionally containing one or more double bonds, an arylcarbonyl or arylalkylcarbonyl group, straight or branched $C_1$-$C_{10}$ alkyloxycarbonyl or cyclic $C_3$-$C_7$ alkyloxycarbonyl optionally containing one or more double bonds, an aryloxycarbonyl or arylalkyloxycarbonyl group, or an amino group.

$R_4$ and $R_5$ are preferably hydrogen.

$R_6$ and $R_7$ are preferably, independently from each other, hydrogen, an alkylcarbonyl, arylcarbonyl, arylalkylcarbonyl, alkoxycarbonyl, arylalkoxycarbonyl group.

More preferably $R_4$, $R_5$, $R_6$, $R_7$ are hydrogen.

An arylcarbonyl or arylalkylcarbonyl group is preferably a phenylcarbonyl or benzylcarbonyl group in which the phenyl portion can be substituted by one to three substituents selected from halogen atoms such as fluorine, chlorine, bromine or iodine and/or methyl, methoxy, trifluoromethyl, trifluoromethoxy, cyano, nitro, aminocarbonyl groups.

A heteroaryl-$C_1$-$C_5$-alkyl group is for example a pyridylalkyl, furanylalkyl, thienylalkyl group; an aryl group is for example a phenyl group or a phenyl substituted as indicated above. A heteroaryl group is for example a pyridyl, furyl, thienyl, thiazolyl, imidazolyl group.

An aryloxycarbonyl or arylalkyloxycarbonyl group is preferably a phenoxycarbonyl and benzyloxycarbonyl group.

Examples of particularly preferred compounds of the invention are:

3-amino-N-[(1S)-2-hydroxy-1-(1H-benzimidazol-4-yl-methyl)-ethyl]propanamide 3-amino-N-[(1S)-2-hydroxy-1-(1H-pyrrol-2-yl-methyl)ethyl]-propanamide 3-amino-N-[(1S)-2-methoxy-1-(1H-imidazol-5-yl-methyl)ethyl]-propanamide 3-(acetylamino)-N-[(1S)-2-hydroxy-1-(1H-imidazol-5-yl-methyl)-ethyl]propanamide 3-amino-N-[(1S)-2-(acetyloxy)-1-(1H-imidazol-5-yl-methyl)ethyl]-propanamide 3-amino-N-[(1R)-2-hydroxy-1-(1H-imidazol-5-yl-methyl)ethyl]-propanamide 3-(propionylamino)-N-[(1S)-2-hydroxy-1-(1H-imidazol-5-yl-methyl)ethyl]propanamide 3-amino-N-[2-hydroxy-1-(1H-imidazol-5-yl-methyl)ethyl]-propanamide 3-amino-N-[(1S)-2-hydroxy-1-(1H-imidazol-5-yl-methyl)ethyl]-propanamide 3-methylamino-N-[(1S)-2-hydroxy-1-(1H-imidazol-5-yl-methyl)-ethyl]propanamide 3-(benzyloxycarbonylamino)-N-[(1S)-2-hydroxy-1-(1H-imidazol-5-yl-methyl)-ethyl]propanamide 3-amino-N-[(1S)-2-hydroxy-1-(4-methyl-1H-imidazol-5-yl-methyl)ethyl]propanamide 3-amino-N-[(1S)-2-hydroxy-1-(4-chloro-1,4-imidazol-5-yl-methyl)-ethyl]-propanamide.

Furthermore, the invention relates to a composition containing an effective amount of one or more compounds of the invention in combination with suitable excipients.

The compounds according to the invention were synthesised by known peptide synthesis methods in solid phase or in solution, reported in the literature, for example in Houben-Weil "Synthesis of peptides and peptidomimetics", vol. E22 a-d, and J. Jones "Amino acid and peptide synthesis". The amino acids used in the synthesis, if not available in already protected form, were suitably functionalised with the necessary protective groups using known methods, such as those reported in T. W. Greene, P. G. M. Wuts "Protective group in Organic Synthesis" and in P. J. Kocienski "Protecting Groups". The amino alcohols used in the synthesis were prepared by reduction of derivatives of the corresponding amino acids using suitable metal or organometal hydrides in inert solvents, and similar procedures were used in the reduction of dipeptide to aminoacylaminoalcohol derivatives.

The end products obtained were purified, when necessary, by one of the known methods, using, for example, crystallisation, chromatographic purification or any other technique required to obtain compounds with the necessary degree of purity.

The pharmacological activity of the compounds according to the invention was determined in vitro by evaluating their carbonyl-quenching activity towards 4-hydroxy nonenal (FINE), which is known for its involvement in numerous disorders.

For the uses considered, the compounds according to the invention are conveniently formulated as conventional pharmaceutical, cosmetic or nutritional compositions suitable for oral, parenteral, topical or transdermal administration.

Examples of these compositions include capsules, tablets, syrups, injectable solutions or suspensions, ointments, suppositories, controlled-release forms and the like, and water-soluble granulates. These compositions, together with conventional carriers and excipients, could also contain other active ingredients which have a complementary activity or are otherwise useful for the treatment/prevention of the disorders in question.

The invention is illustrated in detail by the following examples.

EXAMPLE 1

3-(Benzyloxycarbonylamino) propionyl-L-histidine

A 0.5 L round-bottom flask is loaded with 22.6 g of 3-aminopropionyl-histidine, 150 ml of water and 30 ml of acetone. The solution is adjusted to pH 13.00 with 30% sodium hydroxide, then cooled to 0-5° C., at which temperature 18.7 g of benzyl chloroformate are dropwise added in about 1 h, keeping pH at 12-13 with sodium hydroxide. Afterwards, the mixture is stirred for 15 h at 20-25° C., acidified to pH 2.0-2.5 with 37% hydrochloric acid, then concentrated under vacuum, at 50° C. maximum, carrying out repeated evaporations with isopropanol to a white solid residue. 40 g of a residue are obtained.

$^1$H-NMR (300 MHz, D$_2$O) ppm: 8.38 (s 1H); 7.32 (m 5H); 7.08 (s 1H); 5.05 (m 21-1); 4.40 (m 1H); 3.30 (m 2H); 3.10 (dd 1H); 2.95 (dd 1H); 2.41 (m 2H).

EXAMPLE 2

3-(Benzyloxycarbonylamino)propionyl-L-histidine ethyl ester

A 1 L round-bottom flask, under nitrogen atmosphere, is loaded with 40 g of 3-(benzyloxycarbonylamino) propionyl-L-histidine, 200 g of absolute ethanol and 80 g of an 8M HCl ethanol solution.

The mixture is stirred for 15 h at 20-30° C., monitoring the reaction by TLC, then is concentrated under vacuum, at 40° C. maximum, thus reducing by 80% the starting weight. Then concentration is interrupted, the mixture is cooled to 10-15° C. then, keeping the temperature below 15° C., 100 g of isobutanol, 100 g of methyl tert-butyl ether and 100 g of sodium bicarbonate saturated aqueous solution are added thereto. The mixture is further cooled to 0-5° C., at which temperature the system is adjusted to pH 7.0-7.5 with 30% sodium hydroxide. The mixture is stirred for 30' while temperature returns to 20-25° C., then stirring is interrupted and phases are left to separate for 20'. The aqueous phase is discarded, whereas the organic one is concentrated under vacuum at 50° C. max, to obtain approx. 80 g of a thick oily residue which is used as it is in the subsequent reaction.

EXAMPLE 3

3-(Benzyloxycarbonylamino)-N-[(1S)-2-hydroxy-1-(1H-imidazol-5-yl-methyl)ethyl]propanamide A 1 L round-bottom flask, under nitrogen atmosphere, is loaded with 80 g of the oily residue from Example 2, 100 g of methanol and 300 g of water. The mixture is stirred for 15' at 20-30° C. to complete dissolution. Then 4.24 g of lithium chloride and subsequently 13 g of NaBH$_4$ in portions are loaded during 30 minutes. Afterwards, the mixture is stirred for 15 h at 20-25° C., concentrated under vacuum at 40° C. reducing by 80% the starting weight and finally stripping with isobutanol (4×50 g). The residue is taken up in 100 g of methanol and 200 g of MTBE. The mixture is stirred for 2 h at 20-25° C. Salts are filtered off through Celite, washing with methanol/MTBE (1:2 v/v). The filtrate is concentrated under vacuum, at 50° C. maximum, until constant weight. 52 g of an oily residue are obtained. A sample is purified by silica column chromatography (eluent: CH$_2$Cl$_2$ 80: MeOH 20).

$^1$H-NMR: (300 MHz, DMSO D$_6$) ppm: 7.78 (d, 1H); 7.60 (s 1H); 7.35 (m 5H); 6.78 (s 1H); 5.02 (s 2H); 3.92 (m 1H); 3.35 (m 2H); 3.15 (m 2H); 2.75 (dd 1H); 2.60 (dd 1H); 2.24 (m 2H).

EXAMPLE 4

3-Amino-N-[(1S)-2-hydroxy-1-(1H-imidazol-5-yl-methyl)-ethyl]propanamide

A round-bottom flask under inert atmosphere is loaded with 26 g of the oily product from Example 3, and 100 g of a 1:1 methanol/water mixture. The mixture is stirred to complete dissolution, then added with 2.6 g of 10% Pd/C. A washing cycle is carried out under nitrogen-vacuum, then the mixture is heated to 40° C. and hydrogen is slowly bubbled therein until complete disappearance of the starting product. The mixture is cooled to 30° C. and the catalyst is filtered off through a celite pad, washing twice with a methanol-water mixture. The solvent is evaporated off and the residue is repeatedly taken up with isobutanol and evaporated to obtain 9 g of a white solid.

$^1$H-NMR: (300 MHz, D$_2$O) ppm: 7.55 (s 1H); 6.80 (s 1H); 4.05 (m 1H); 3.55 (dd 1H); 3.45 (dd 1H); 2.80-2.50 (mm 4H); 2.24 (m 2H).

Pharmacological Tests

The carbonyl-quenching activity of a selected series of compounds to which this patent relates has been demonstrated in vitro by incubating HNE (50 μM) with the molecule under study (1 mM), in phosphate buffer (10 mM), pH 7.4, at 37° C. The activity was evaluated one, two and three hours after incubation, determining the residual HNE content by reverse-phase chromatography as previously described by Aldini G. et al. [Biochem Biophys Res Commun. 2002 Nov. 15; 298(5):699-706]. The carbonyl-quenching activity is evaluated on the basis of the percentage of HNE reacted, compared with the HNE content in the absence of the molecule to be tested. By way of example, the activity of compound 3-amino-N-[(1S)-2-hydroxy-1-(1H-imidazol-5-yl-methyl)ethyl]propanamide proved to be 1.66 times greater than that of β-alanyl histidine taken as the standard substance.

The stability of the compound in human serum, rat plasma, rat liver fraction S9000 and human liver fraction S9000 was also evaluated by incubation at 37° C. and successive sampling after 0.15 and 30 min, 1 h and 2 h. The samples taken from each matrix, suitably treated, were analysed by HPLC-MS, and between 85 and 93% of the initial value was recovered after 2 h. A preliminary toxicological study in the rat with intraperitoneal administration was also performed on the same compound (single dose 100 mg/kg), IV (3 consecutive doses 3, 10 and 30 mg/kg) and per os (gavage, 100 mg/kg/day for 7 days), and no toxic effects were observed.

The invention claimed is:

1. Compounds of general formula I,

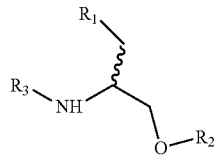

wherein:
R₁ is an optionally condensed, optionally substituted nitrogen heterocyclic ring, containing one or more nitrogen atoms, at least one of which is an —NH— group;
R₂ is hydrogen, straight, branched or cyclic C1-C10 alkyl, straight, branched or cyclic C1-C8 alkylcarbonyl, an optionally substituted arylcarbonyl or arylalkylcarbonyl group; and
R₃ is a group of formula II,

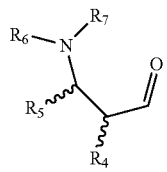

wherein
R₄ and R₅, which can be the same or different, are hydrogen, straight or branched C1-C8 alkyl or cyclic C3-C7 alkyl, aryl-C1-C5 alkyl or heteroaryl-C1-C5-alkyl, or an aryl or heteroaryl group; and
R₆ and R₇, which can be the same or different, are hydrogen, straight, branched or cyclic C1-C8 alkyl, straight or branched C1-C20 alkylcarbonyl or cyclic C3-C7 alkylcarbonyl optionally containing one or more double bonds, an arylcarbonyl or arylalkylcarbonyl group, straight or branched C1-C10 alkyloxycarbonyl or cyclic C3-C7 alkyloxycarbonyl optionally containing one or more double bonds, an aryloxycarbonyl or arylalkyloxycarbonyl group, an amino group, or a group of general formula III,

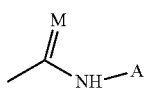

wherein M is nitrogen, oxygen or sulfur and A is hydrogen or an amino group;
the enantiomers, diastereomers or mixtures thereof.

2. The compound according to claim 1, wherein R₁ is selected from the group consisting of optionally substituted imidazole, pyrrole, pyrazole, indole, isoindole, indazole, and benzimidazole.

3. The compound according to claim 2, wherein R₁ and R₂ are as previously defined, and R₃ is a group of general formula II,

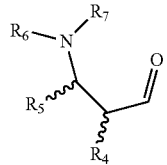

wherein
R₄, R₅, are as previously defined,
R₆ and R₇, which can be the same or different, are hydrogen, straight or branched C1-C10 alkylcarbonyl or cyclic C3-C7 alkylcarbonyl optionally containing one or more double bonds, an arylcarbonyl or arylalkylcarbonyl group, straight or branched C1-C10 alkyloxycarbonyl or cyclic C3-C7 alkyloxycarbonyl optionally containing one or more double bonds, an aryloxycarbonyl or arylalkyloxycarbonyl group, or an amino group.

4. The compound according to claim 3, wherein R₄ and R₅ are hydrogen.

5. The compound according to claim 4, wherein R₁ is an imidazole ring optionally substituted at the 2- or 4-position by a straight, branched or cyclic C1-C6 alkyl group or by a halogen atom.

6. The compound according to claim 5, wherein:
R₂ is hydrogen, straight, branched or cyclic C1-C8 alkylcarbonyl, an arylcarbonyl or arylalkylcarbonyl group; and
R₃ is a group of formula II, wherein R₄ and R₅ are hydrogen, and R₆ and R₇ are independently hydrogen, or an alkylcarbonyl, arylcarbonyl, arylalkylcarbonyl, alkyloxycarbonyl, arylalkyloxycarbonyl group.

7. The compound according to claim 6, wherein R₂ is hydrogen.

8. The compound according to claim 6, wherein R₃ is a group of formula II and R₄, R₅, R₆, R₇ are hydrogen.

9. The compound according to claim 1, selected from the group consisting of:
3-amino-N-[(1S)-2-hydroxy-1-(1H-benzimidazol-4-yl-methyl)-ethyl]propanamide,
3-amino-N-[(1S)-2-hydroxy-1-(1H-pyrrol-2-yl-methyl)ethyl]-propanamide,
3-amino-N-[(1S)-2-methoxy-1-(1H-imidazol-5-yl-methyl)ethyl]-propanamide,
3-(acetylamino)-N-[(1S)-2-hydroxy-1-(1H-imidazol-5-yl-methyl)-ethyl]propanamide,
3-amino-N-[(1S)-2-(acetyloxy)-1-(1H-imidazol-5-yl-methyl)ethyl]-propanamide,
3-amino-N-[(1R)-2-hydroxy-1-(1H-imidazol-5-yl-methyl)ethyl]-propanamide,
3-(propionylamino)-N-[(1S)-2-hydroxy-1-(1H-imidazol-5-yl-methyl)ethyl]propanamide,
3-amino-N-[2-hydroxy-1-(1H-imidazol-5-yl-methyl)ethyl]-propanamide,
3-amino-N-[(1S)-2-hydroxy-1-(1H-imidazol-5-yl-methyl)ethyl]-propanamide,
3-methylamino-N-[(1S)-2-hydroxy-1-(1H-imidazol-5-yl-methyl)-ethyl]propanamide,
3-(benzyloxycarbonylamino)-N-[(1S)-2-hydroxy-1-(1H-imidazol-5-yl-methyl)ethyl]propanamide,
3-amino-N-[(1S)-2-hydroxy-1-(4-methyl-1H-imidazol-5-yl-methyl)ethyl]propanamide, and
3-amino-N-[(1S)-2-hydroxy-1-(4-chloro-1H-imidazol-5-yl-methyl)ethyl]propanamide.

10. A pharmaceutical composition, comprising an effective amount of one or more compounds according to claim 1 in combination with suitable excipients, wherein the effective amount is sufficient to block secondary products of oxidative lipid stress.

* * * * *